(12) United States Patent
Yin et al.

(10) Patent No.: US 11,312,744 B2
(45) Date of Patent: Apr. 26, 2022

(54) METHOD FOR PURIFYING LONG CHAIN POLYPEPTIDE

(71) Applicant: HYBIO PHARMACEUTICAL CO., LTD., Shenzhen (CN)

(72) Inventors: Chuanlong Yin, Shenzhen (CN); Pengcheng Mi, Shenzhen (CN); Anjin Tao, Shenzhen (CN); Jiancheng Yuan, Shenzhen (CN)

(73) Assignee: HYBIO PHARMACEUTICAL CO., LTD., Shenzhen (CN)

( * ) Notice: Subject to any disclaimer, the term of this patent is extended or adjusted under 35 U.S.C. 154(b) by 0 days.

(21) Appl. No.: 15/733,862

(22) PCT Filed: May 30, 2018

(86) PCT No.: PCT/CN2018/089034
§ 371 (c)(1),
(2) Date: Nov. 30, 2020

(87) PCT Pub. No.: WO2019/227342
PCT Pub. Date: Dec. 5, 2019

(65) Prior Publication Data
US 2021/0230216 A1    Jul. 29, 2021

(51) Int. Cl.
| C07K 1/20 | (2006.01) |
| C07K 14/435 | (2006.01) |
| C07K 14/575 | (2006.01) |
| C07K 14/58 | (2006.01) |
| C07K 1/16 | (2006.01) |

(52) U.S. Cl.
CPC .................. *C07K 1/16* (2013.01); *C07K 1/20* (2013.01); *C07K 14/435* (2013.01); *C07K 14/575* (2013.01); *C07K 14/58* (2013.01)

(58) Field of Classification Search
CPC .......... C07K 1/16; C07K 1/20; C07K 14/435; C07K 14/575; C07K 14/58
See application file for complete search history.

(56) References Cited

FOREIGN PATENT DOCUMENTS

| CN | 104371018 A | 2/2015 |
| CN | 105949284 A | 9/2016 |
| CN | 106519009 A | 3/2017 |

*Primary Examiner* — Jeffrey E. Russel
(74) *Attorney, Agent, or Firm* — Bayramoglu Law Offices LLC

(57) ABSTRACT

A method for purifying a long chain polypeptide includes: 1) purification step: connecting two chromatographic columns in series to separate a crude product, in which the particle size of a packing in an upstream chromatographic column is larger than that in a downstream chromatographic column; optionally, the method further includes step 2): using the upstream chromatographic column in step 1) for a salt conversion, loading the target peak product obtained in step 1) and rinsing with 95-85% of the A2 and 5-15% of the B for 15-30 min for a desalination, wherein A2 phase is an acetic acid aqueous solution with a volume ratio of 0.05%-0.2%; B phase is an organic phase acetonitrile, and the detection wavelength is 230 nm.

8 Claims, 11 Drawing Sheets
Specification includes a Sequence Listing.

METHOD FOR PURIFYING LONG CHAIN POLYPEPTIDE

CROSS REFERENCE TO THE RELATED APPLICATIONS

This application is the national phase entry of International Application No. PCT/CN2018/089034, filed on May 30, 2018, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBBJCH041-PKG Sequence Listing.txt, created on 07/12/2021 and is 624 bytes in size.

TECHNICAL FIELD

The present invention relates to the technical field of drug analysis, and in particular, to a method for purifying a long chain polypeptide drug.

BACKGROUND

Ularitide is a natriuretic peptide developed by Cardiorentis (AG) and composed of 32 amino acid residues. Ularitide was originally isolated from urine by Schulz-Knappe et al. in 1988 as a renal natriuretic peptide belonging to the atrial natriuretic peptide (ANP) family, which is mainly used to treat acute heart failure.

The molecular formula of ularitide is as follows (SEQ) ID NO: 1).

```
                              ┌─────────────S─S──────────────┐
H—Thr-Ala-Pro-Arg-Ser-Leu-Arg-Arg-Ser-Ser-Cys-Phe-Gly-Gly-Arg-Met-Asp-Arg-Ile-Gly-Ala-Gln-Ser-Gly-Leu-Gly-Cys-Asn-Ser-Phe-Arg-Tyr—OH
```

Epidemiological data show that the number of heart failure patients worldwide has reached 22.5 million, and is still increasing at the rate of 2 million per year. And the 5-year survival rate of heart failure patients is substantially equal to that of malignant tumor patients. 20% of heart failure patients will be hospitalized again within 30 days after discharge, which adds medical and insurance expenses. The prevalence of heart failure in adults in China is 0.9%, of which 0.7% for men and 1.0% for women. Currently, there are still about 4 million heart failure patients among adults aged 35-74 years old, and the number is increasing year by year.

Common causes include coronary heart disease, hypertension, cardiomyopathy and (or) valvular disease, diabetes, and others, among which coronary artery disease is an important factor in heart failure. According to statistics, the global annual expenditure on heart failure is 108 billion US dollars. According to a large-scale epidemiological survey in 2003, the prevalence rate of heart failure among adults in mainland China has reached 0.9%, and there are about 4.5 million heart failure patients. Heart failure can be divided into acute heart failure and chronic heart failure. In the past 10 years, there have been 10 million cases of emergency treatment for acute heart failure in the United States, and about 15-20% are first diagnosed with heart failure, while most are due to deterioration.

All diseases causing chronic heart failure can lead to acute heart failure. With the increasing number of chronic heart failure patients, chronic cardiac decompensation and acute heart failure episodes have also become the leading cause of hospitalization in patients with heart failure. The annual incidence rate of heart failure is 0.23%-0.27%. The prognosis of acute heart failure is very poor. The in-hospital mortality rate is 3%, the 60-day mortality rate is 9.6%, and the 3-year and 5-year mortality rates are as high as 30% and 60%, respectively. The mortality rate of acute heart failure caused by acute myocardial infarction is higher. The in-hospital mortality rate of patients with acute pulmonary edema is 12%, and the one-year mortality rate is 30%. Therefore, ularitide has a broad market prospect.

The existing peptide purification is mainly achieved by high performance liquid phase system, and the organic phase is acetonitrile, methanol, etc. The use amount of the organic phase is generally substantial, resulting in a large amount of waste liquid discharge. Waste liquid recovery is difficult and dangerous. With the extension of peptide sequence, the discharge amount of waste liquid will be larger, the purification cycle will be longer, and the enterprise cost will be higher. Environmental protection, safety and cost problems have restricted the development of pharmaceutical enterprises. A purification method to reduce the enterprise cost and discharge of waste liquid is urgently needed to minimize the risk of organic waste liquid storage.

Ularitide is mainly used for acute heart failure, so its quality is particularly important. Ularitide has a long peptide sequence, and it has to undergo an oxidation step in the intermediate process, resulting in more impurities. In order to improve the safety of drugs, high purity is required for existing polypeptide drugs. Most drugs are required to have a purity greater than 99%, and single impurity is also required to be controlled to be less than 0.10%. The traditional purification process generally needs two steps of purification and one step of salt conversion to meet this standard. However, the yield is particularly low, and labor cost, environmental cost and product cost are high.

The purification of polypeptides is mainly carried out by reversed phase chromatography, and the stationary phases generally include C18, C8, C4, C1, etc. Additionally, polymer packings and even other reversed-phase packings may be used for purification, but the purification process remains essentially unchanged regardless of the type of packings used. There are two basic processes. One process is to fill a column with one kind of packings under a high pressure. The length of the column is generally about 25 cm and the particle size is mostly 10 μm. After purification under different chromatographic conditions, the unqualified parts are recovered and finally qualified products are obtained.

The other process is to fill a column with different types of packings under a high pressure. The length of the column is about 25 cm and the particle size is generally 10 μm. After purification under different chromatographic conditions, the unqualified parts are recovered and purified, and finally qualified products are obtained. For peptides with a short peptide sequence, the above two processes can be completed by one step of purification, while for peptides with a peptide sequence larger than 25 amino acids, two steps of purification are needed, along with desalination or salt conversion, it takes three steps to complete.

The disadvantages of the two processes are that purifying a large-scale product requires a substantial period of time, and the unqualified intermediates need to be recycled many times to get qualified products. Because of the need for recovery and purification, the cycle is prolonged, the amount of organic solvent used and the discharge of waste liquid increase, which adds to cost, compromises quality and increases the organic solvent risk coefficient.

SUMMARY

The present invention provides a new purification method, which can improve the purity of a product, so that the purity of the product is more than 99%, the single impurity content is less than 0.10%, and the cost and environmental protection concerns can be greatly reduced.

The present invention provides a new purification method, which is different from the traditional purification method and addresses the disadvantages of the traditional purification method, such as high cost, long cycle and large discharge of waste liquid caused by multiple recovery, thus greatly improving the yield and being easy to increase production.

One aspect of the present invention provides a method for purifying a long chain polypeptide, including the following steps:

1) purification step: connecting two chromatographic columns in series to separate a crude product; wherein, a packing in the chromatographic columns in step 1) is at least one selected from the group consisting of C18 silica gel packing, C8 silica gel packing, C4 silica gel packing and a polymer packing; a length of an upstream column is 8-20 cm; a length of a downstream column is 8-20 cm;

mobile phases in step 1): A1 phase is a buffered salt solution with a pH value of 2-3; preferably, the buffered salt solution is at least one selected from the group consisting of ammonium sulfate, potassium dihydrogen phosphate, disodium hydrogen phosphate and dipotassium hydrogen phosphate; B phase is an organic phase, and the organic phase is acetonitrile, methanol, isopropanol and ethanol; a molar concentration of the buffered salt solution is 20 mM-150 mM, and a detection wavelength is 230 nm;

step 1) includes a gradient elution: A1%: 95/6-55%, B %: 5/6-45%, and an elution time is 30-120 min; in the elution process, when an outflow peak of the upstream chromatographic column is an impurity peak, the corresponding mobile phase is discarded; when the outflow peak of the upstream chromatographic column is a target peak, a chromatographic pump connected to a three-way mixer arranged in the middle of the upstream chromatographic column and the downstream chromatographic column is opened, 10% purified water is input, a ratio of the organic phase in the mobile phase is reduced, a real-time dilution is performed, and then the organic phase enters into the downstream chromatographic column after the real-time dilution;

optionally, the method further includes step 2) of salt conversion:

step 2): using the upstream chromatographic column in step 1) for salt conversion, wherein, A2 phase is an acetic acid aqueous solution with a volume ratio of 0.05%-0.2%; B phase is the organic phase, and the organic phase is the acetonitrile, the methanol, the isopropanol and the ethanol; and the detection wavelength is 230 nm;

step 2) includes: loading a target peak product obtained in step 1) and washing with 95% of the A2 and 5% of the B for 15-30 min for a desalination;

then performing a gradient elution for 10-30 min for the salt conversion to collect a target product; A2%: 95/6-55%, B %: 5/6-45%.

In the technical solution of the present invention, the long chain polypeptide is selected from a long chain polypeptide with more than 35 amino acids, and is preferably one selected from the group consisting of ularitide, liraglutide, semaglutide, thymalfasin, abaloparatide and lixisenatide.

In the technical solution of the present invention, in step 1), a packing in the upstream chromatographic column is C18 silica gel packing having a particle size of 10 μm, and the length of the upstream chromatographic column is 10-15 cm; and a packing in the downstream chromatographic column is C18 silica gel packing having a particle size of 5 μm, and the length of the downstream chromatographic column is 10-15 cm.

In the technical solution of the present invention, step 1) includes the gradient elution: A %: 85/6-65%, B %: 15%-55%, and the elution time is 50-70 min.

In the technical solution of the present invention, the pH value of the A1 phase is 2.2-2.8.

In the technical solution of the present invention, A2 phase is an ammonium acetate solution with the volume ratio of 0.1%-0.4%.

In the technical solution of the present invention, in step 2), the desalination is performed with 95% of the A2 and 5% of the B for 15-30 min.

In the technical solution of the present invention, in step 2), the gradient elution is performed for 10-30 min for the salt conversion to collect the target product; A2%: 85%-65%, B %: 15%-35%.

In the technical solution of the present invention, the real-time dilution is as follows: before the target peak product enters the downstream chromatographic column, 10% purified water is input through a third pump to reduce the ratio of the organic phase.

A new purification method, wherein two different types of chromatographic columns are arranged simultaneously. The first column is 10 μm C18, and the second column is 5 μm C18. The lengths of the chromatographic columns are both 10-15 cm considering the column pressure, column effect and the comprehensive cost of packings, and then the chromatographic columns are connected in series. For the purification of ularitide, the first column with larger particle size is mounted in front of the second column with smaller particle size. Then, an oxidized ularitide liquid is purified by the columns. After purification and salt conversion, a purified ularitide is obtained.

A new method for purifying ularitide, wherein two columns are respectively filled with two different types of packings, and then the two columns are connected in series. The method includes a first step of purification and a second step of salt conversion. In the first step, a buffered salt solution with a predetermined concentration and a predetermined pH is used as A1 phase, and acetonitrile is used as B phase. In the second step, acetic acid with a predetermined concentration is used as A2 phase and acetonitrile is used as B phase. The salt conversion is performed by high performance liquid chromatography (HPLC) with a gradient elution. A solution is collected and lyophilized to obtain ularitide acetate.

The peptide chain of ularitide is long, and there are numerous impurities in the synthesis, and it contains amino acids such as Ser which are easily isomerized during the synthesis, resulting in isomeric impurities in the crude peptides. By the new purification method of the present invention, two different types of packings are connected in series for the purification, and the two different types of packings have different separation capabilities. After the purification is performed in the first column, the target peak product does not flow out of the first column, and before entering the downstream chromatographic column, 10% purified water is input by the third pump to reduce the ratio of the organic phase, and then the target peak product enters the second column for the second separation.

The traditional purification process generally needs two steps of purification, which can be completed by only one step of purification in the present invention. Furthermore, the purification method of the present invention reduces the risk of affecting product quality such as intermediate processing, precipitation and denaturation caused by intermediate storage, which can save time and effort.

The purification method of the present invention can separate and remove the isomeric impurities and other impurities that are difficult to separate in the crude peptides, and then uses the reversed-phase HPLC method to convert into acetate, and finally improves the yield and purity of the product.

Meanwhile, the present invention overcomes the shortcomings that traditional purification methods are time consuming, labor intensive and pollutant producing. The present invention provides a new method of purification that is easy to operate, which is beneficial to achieving large-scale preparation.

As an optimization, the molar concentration of the buffered salt in the mobile phase A1 of the HPLC method of the present invention is 20 mM-150 mM, and the volume ratio of the acetic acid in the mobile phase A2 is 0.05%-0.2%.

As an optimization, a range of the pH value of the mobile phase A1 of the HPLC method of the present invention is 2.2-2.8.

As an optimization, the buffered salt is at least one selected from the group consisting of ammonium sulfate, potassium dihydrogen phosphate, disodium hydrogen phosphate and dipotassium hydrogen phosphate.

As an optimization, the mobile phase B of the HPLC method is acetonitrile.

As an optimization, the stationary phases of the HPLC method are octadecyl, and the particle sizes are 5 μm and 10 μm.

Advantages

Connecting columns in series for purification utilizes two kinds of packings with different separation capabilities to purify. Two separations are realized without changing column length, reducing the recovery times, shortening the cycle, and reducing the use amount in the organic phase. Moreover, the operation is simple and easily scalable. A major advantage over prior methods is time-saving and cost-saving, especially for polypeptides with a peptide chain length larger than 35 because such polypeptides require multiple steps of purification and recovery. The effect will be more prominent. The main reason is that the longer the peptide chain is, the more hydrophobic it is, the more organic phase is used when eluting, and coupled with multiple recovery, so the amount of waste liquid is particularly large.

Embodiments are as follows:

Purification is performed by chromatographic columns of the following specifications: 5 cm×25 cm (column diameter×column length), 10 cm×25 cm, 15 cm×25 cm.

DETAILED DESCRIPTION OF THE EMBODIMENTS

Figure 1:
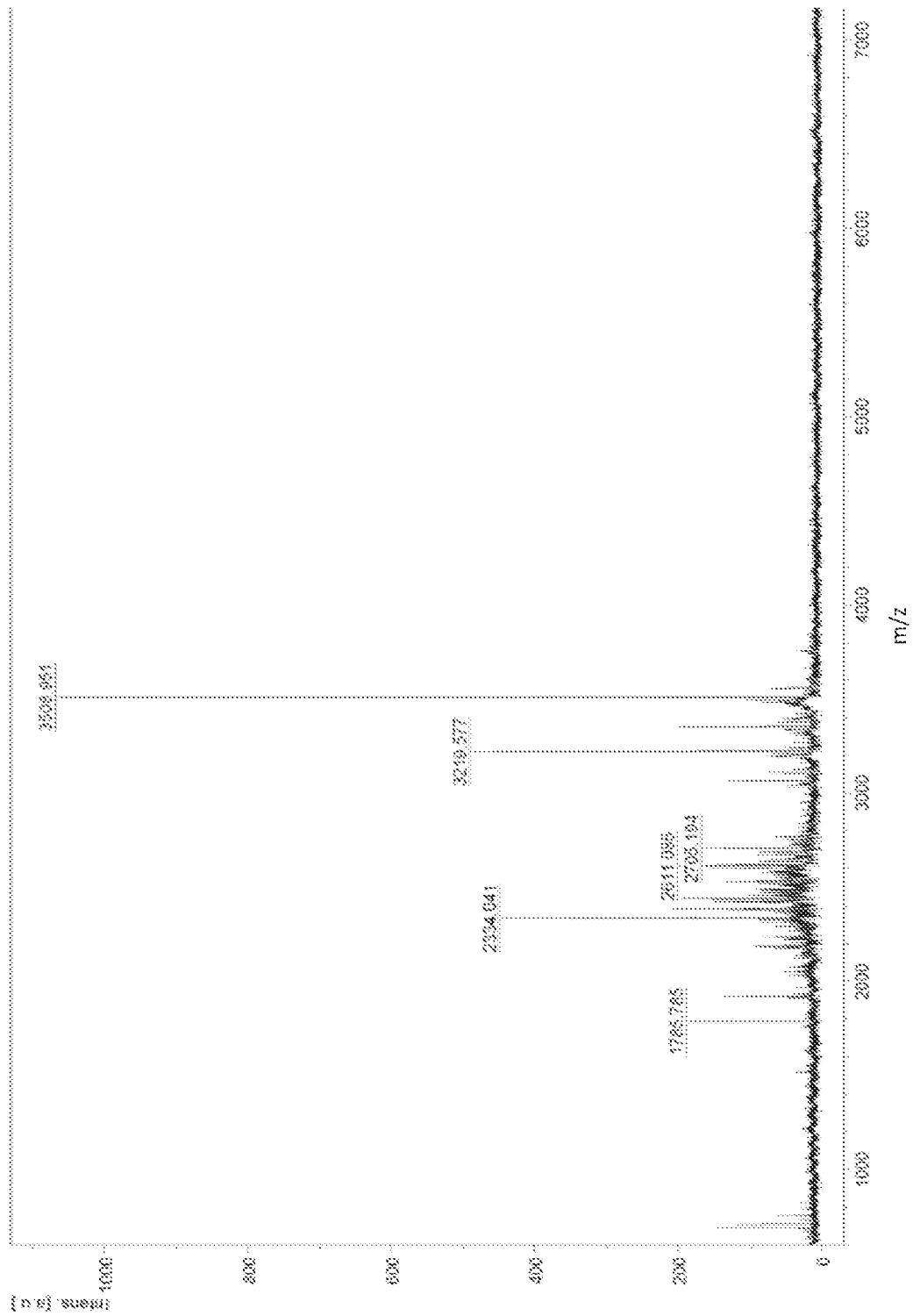
FIG. 1 is a diagram showing a mass spectrum of linear crude peptides.
Figure 2:
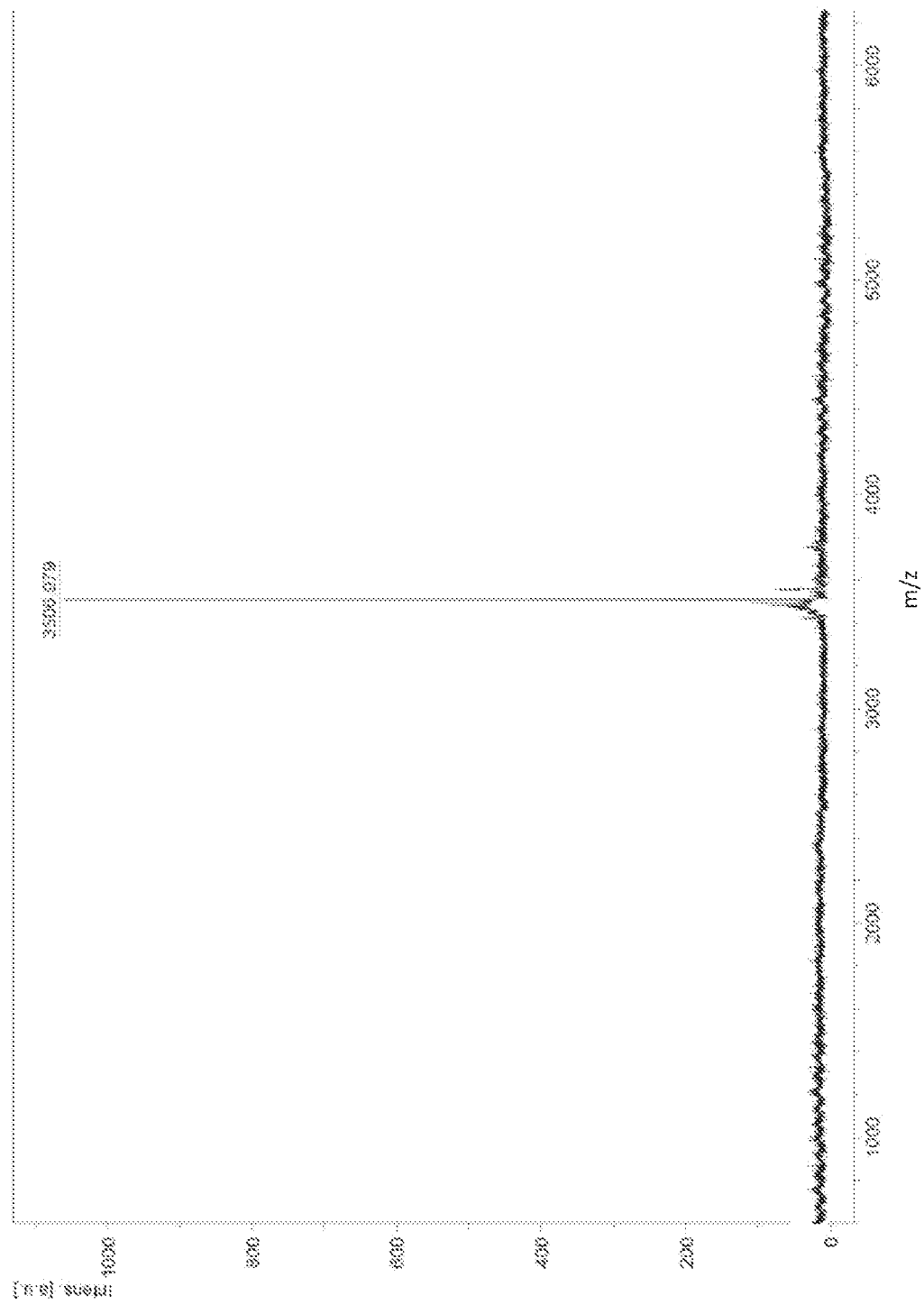
FIG. 2 is a diagram showing a mass spectrum of purified peptides.
Figure 3:
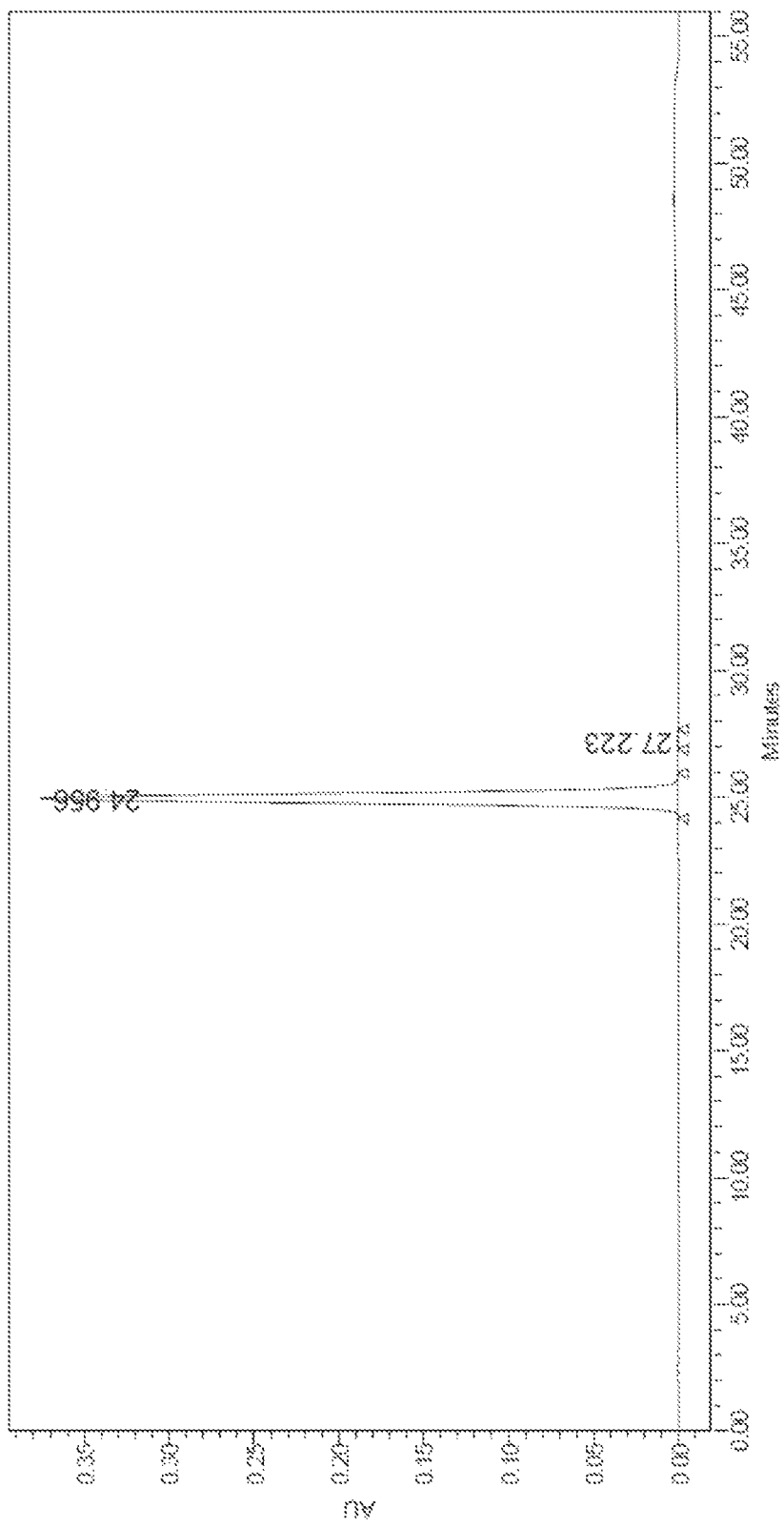
FIG. 3 is a diagram showing an HPLC result of a pure product in embodiment 1.
Figure 4:
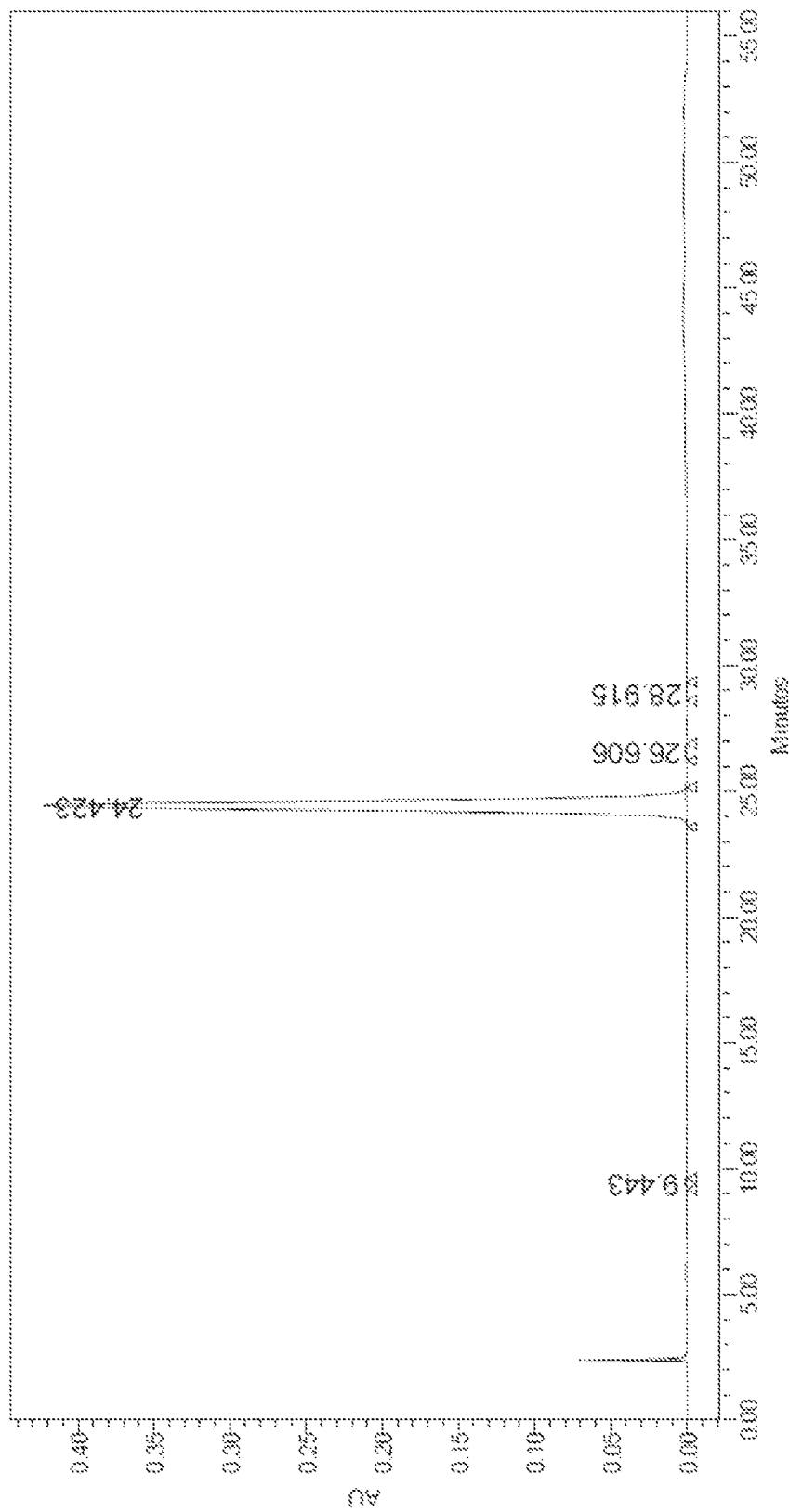
FIG. 4 is a diagram showing an HPLC result of a pure product in embodiment 2.
Figure 5:
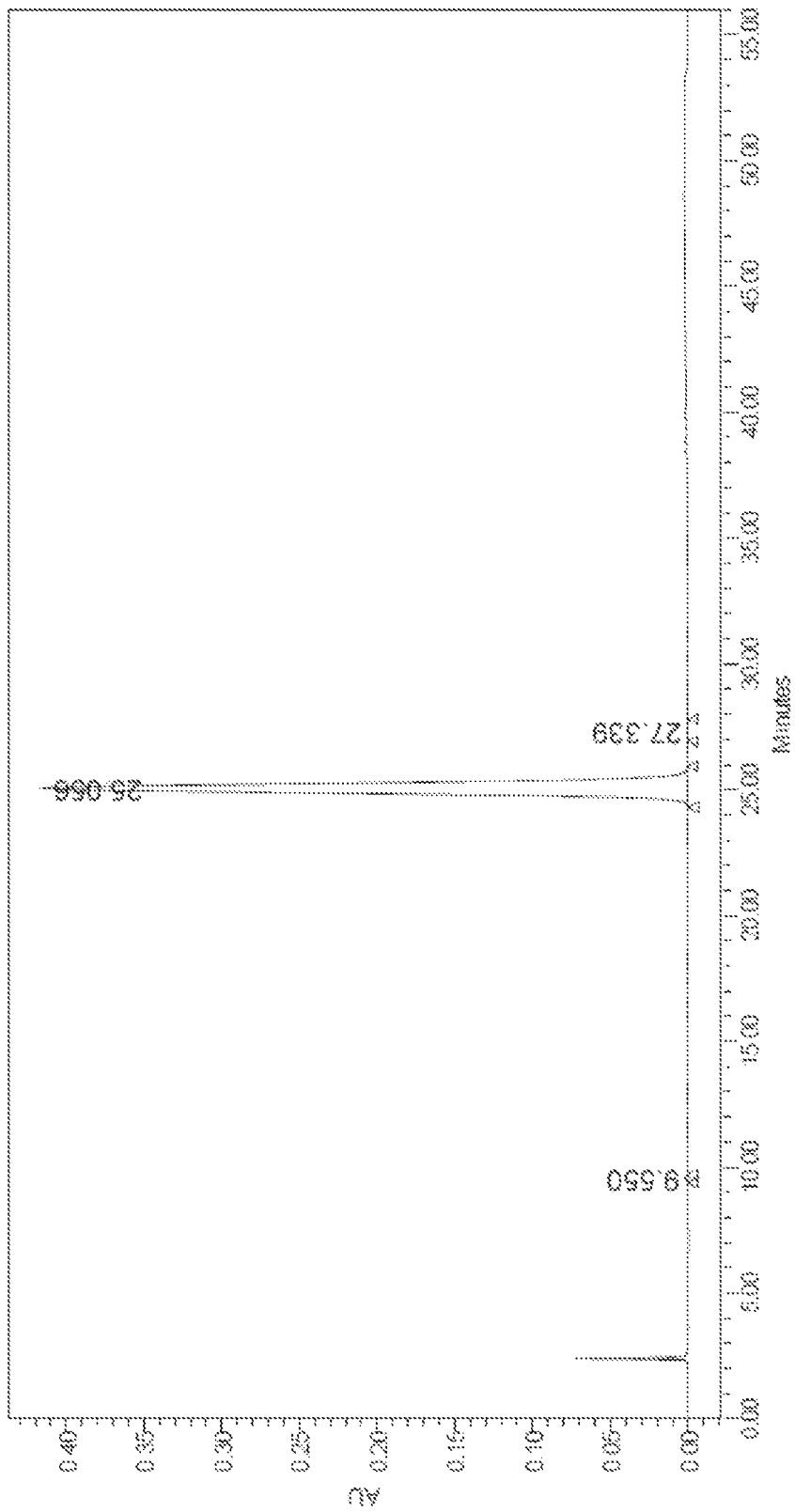
FIG. 5 is a diagram showing an HPLC result of a pure product in embodiment 3.
Figure 6:
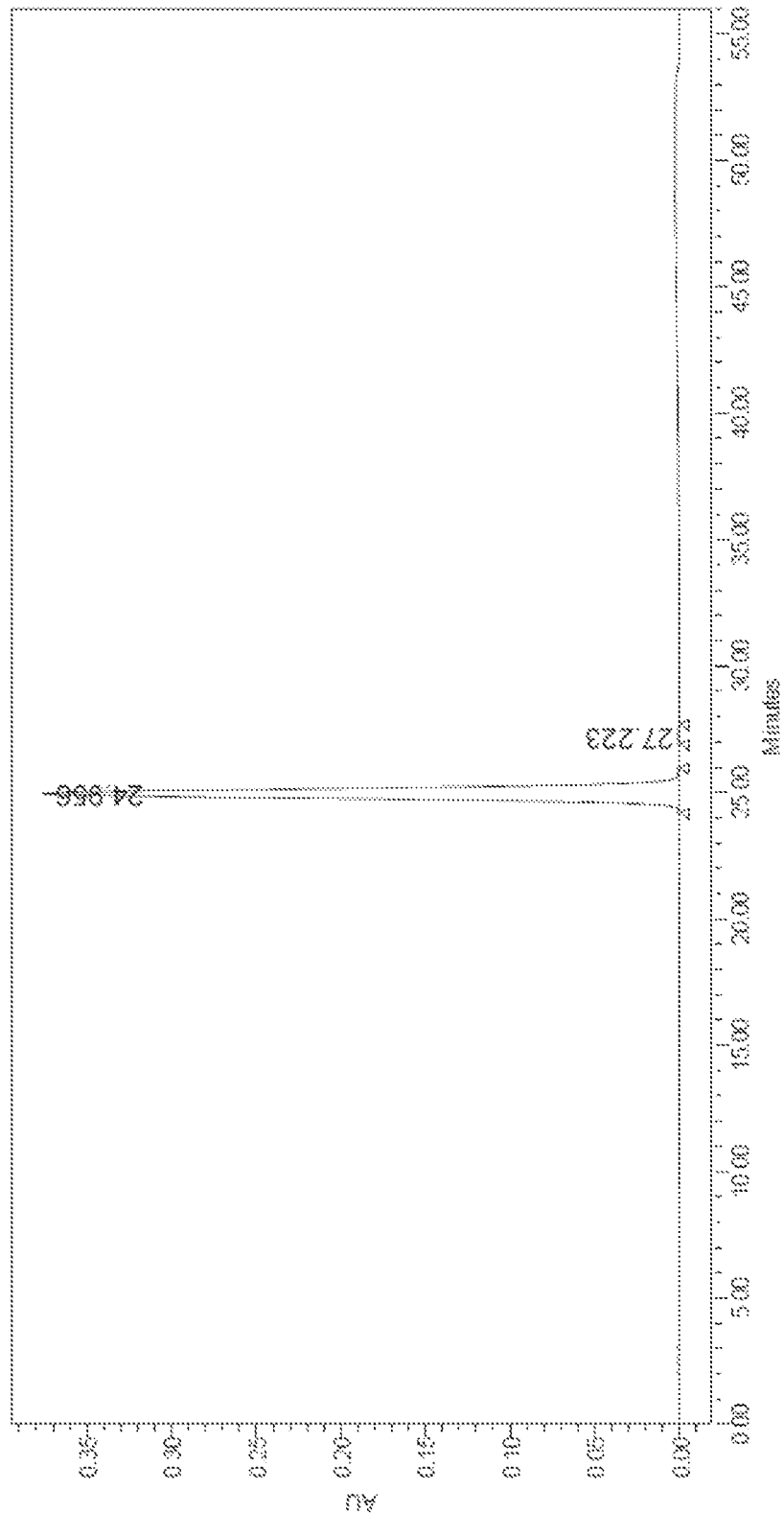
FIG. 6 is a diagram showing an HPLC result of a pure product in embodiment 4.
Figure 7:
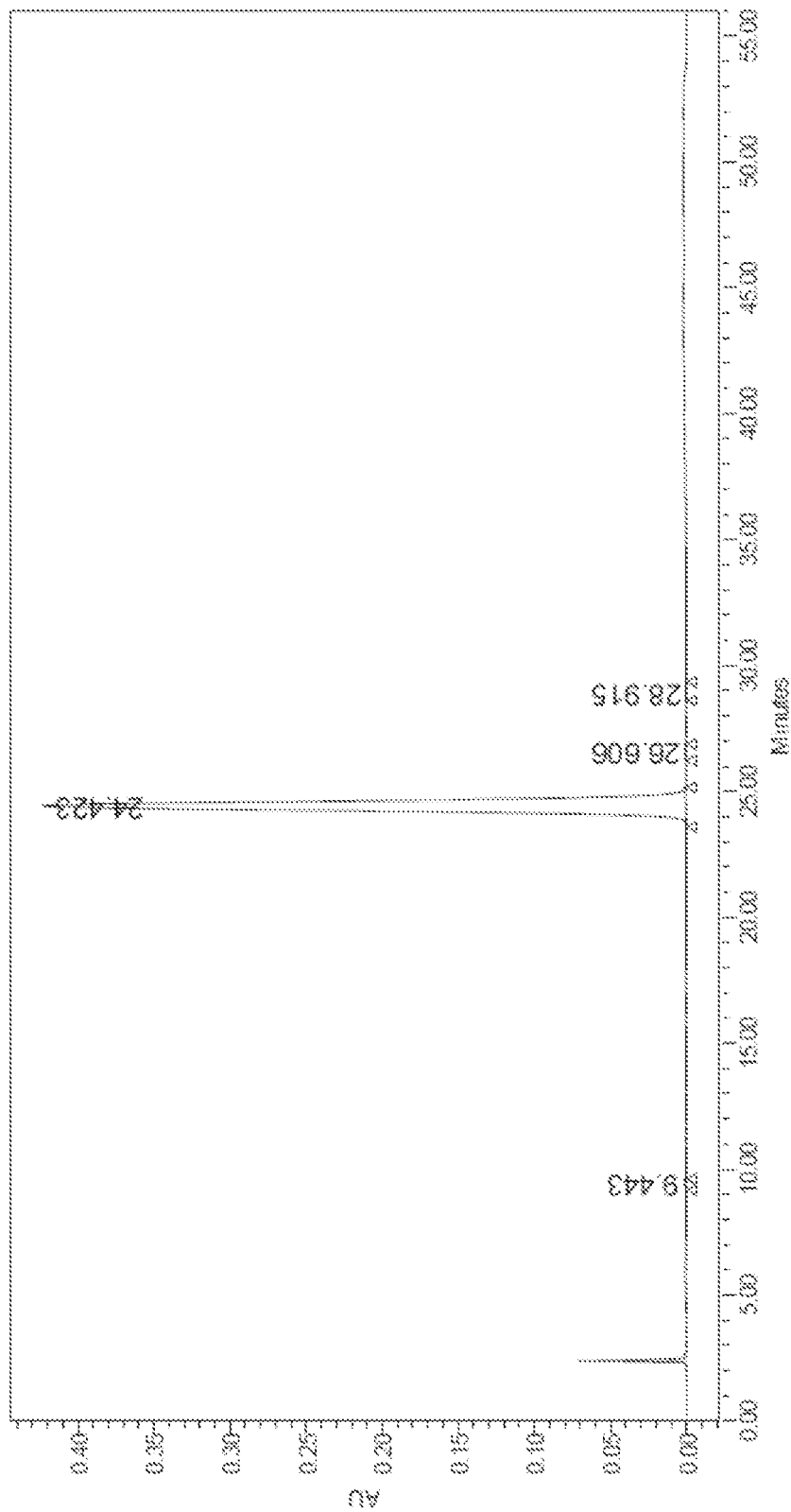
FIG. 7 is a diagram showing an HPLC result of a pure product in embodiment 5.
Figure 8:
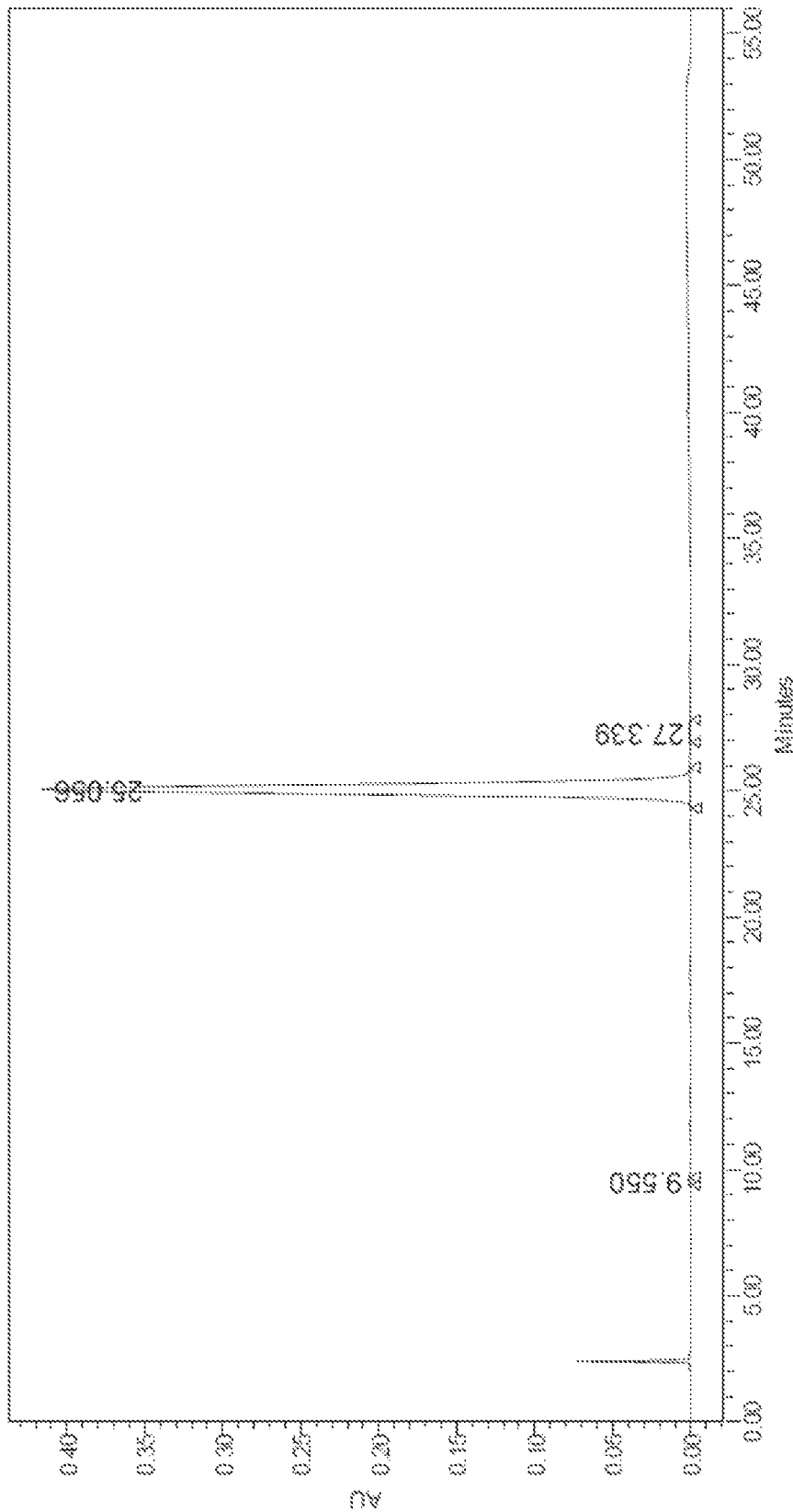
FIG. 8 is a diagram showing an HPLC result of a pure product in embodiment 6.
Figure 9:
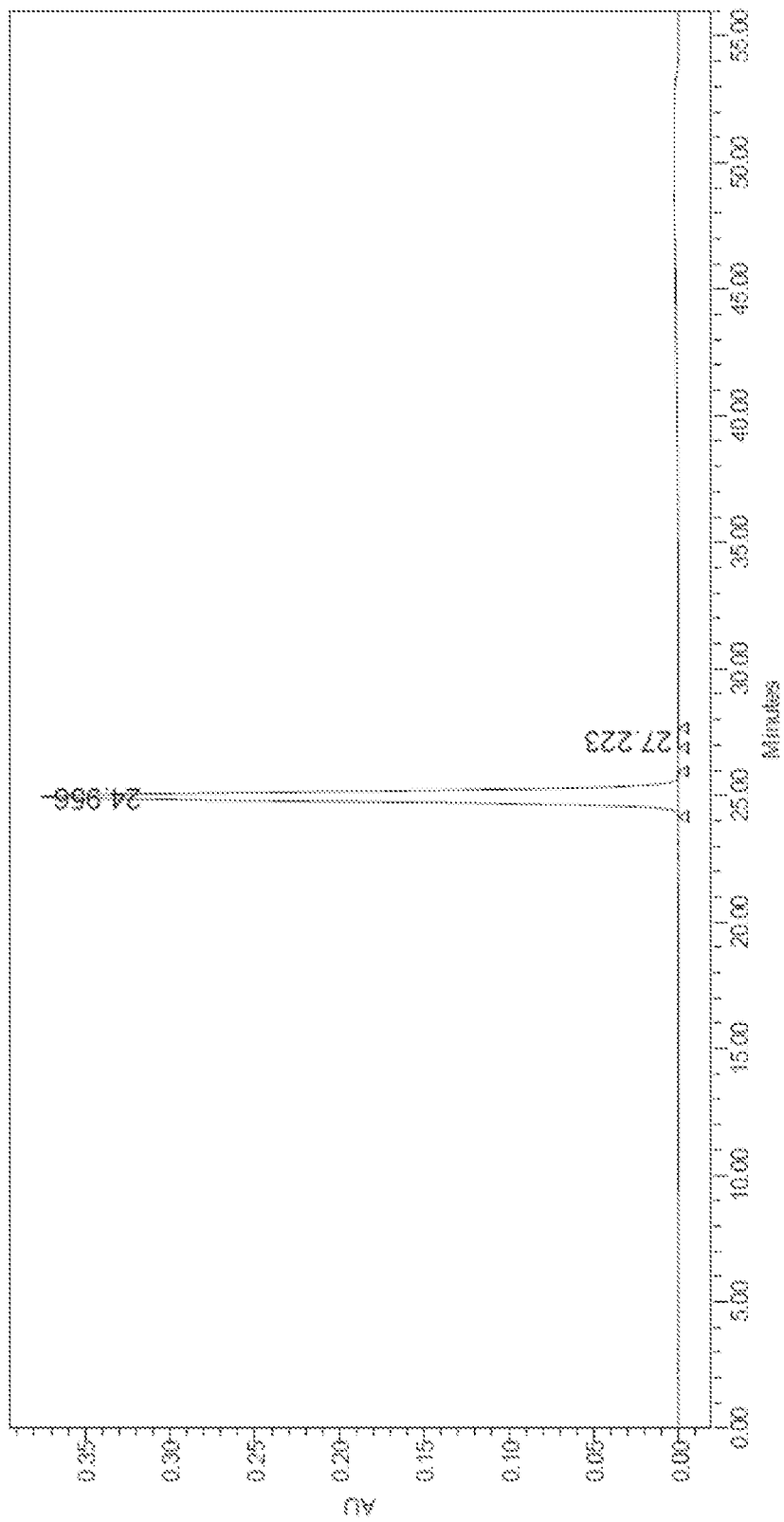
FIG. 9 is a diagram showing an HPLC result of a pure product in embodiment 7.
Figure 10:
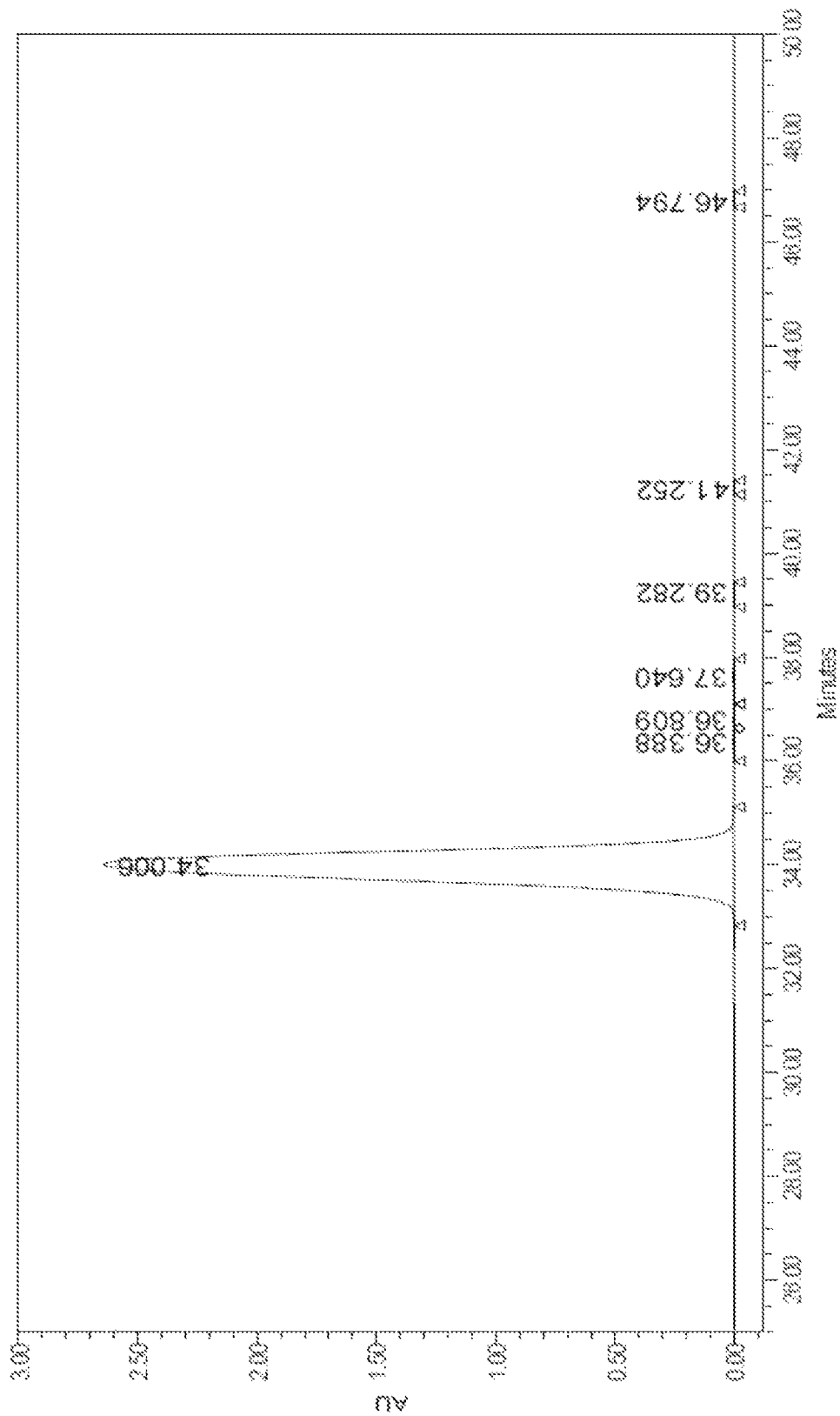
FIG. 10 is a diagram showing an HPLC result of a pure product in embodiment 8.
Figure 11:
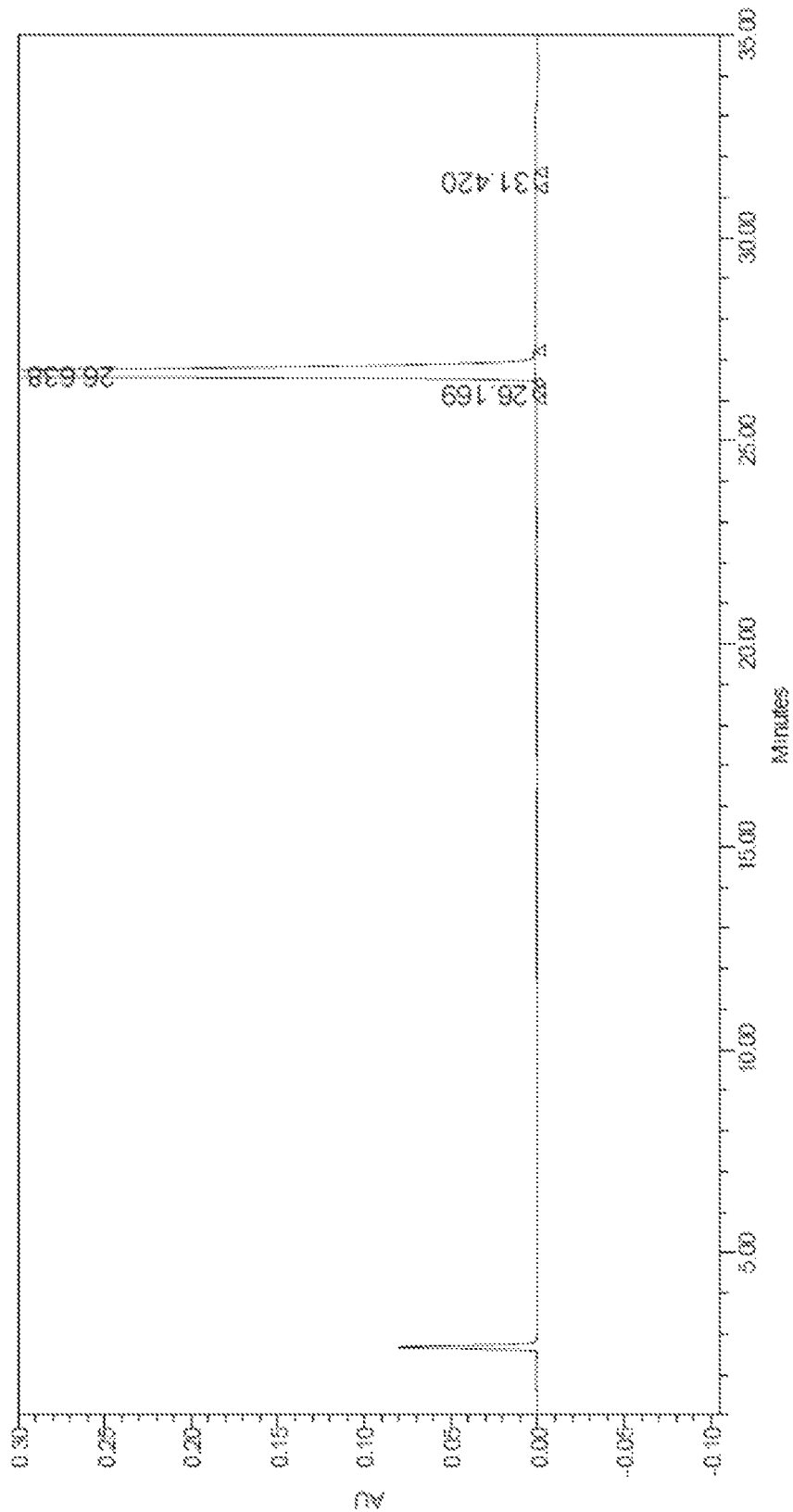
FIG. 11 is a diagram showing an HPLC result of a pure product in embodiment 9.

Embodiment 1: Purification of Crude Ularitide 2.0 g of linear crude ularitide is dissolved and filtered, and a filtrate is collected for use.

1. Purification conditions: chromatographic columns: a chromatographic column filled with a stationary phase C18 silica gel packing with a particle size of 10 μm is used as the column 1, and the diameter and length of the column is 5 cm×10 cm; a chromatographic column filled with a stationary phase C18 silica gel packing with a particle size of 5 μm is used as the column 2, and the diameter and length of the column is 5 cm×15 cm.

Step 1: mobile phases: A1 phase: the pH value of a potassium dihydrogen phosphate solution (50 mmol/L) is adjusted to 2.2 with phosphoric acid; B phase: chromatographic grade acetonitrile; the flow rate is 60-80 ml/min, and the detection wavelength is 230 nm.

A linear crude ularitide solution is loaded and eluted for 50-70 min with the following gradient: A1%: 85/6-65%, B %: 15%-35%. In the elution process, the waste liquid is discarded if an impurity peak appears during the separation through the chromatographic column 1. When a target product peak comes out, the target product is subjected to a real-time dilution by a third pump connected to a three-way mixer and then enters into the column 2 for a secondary separation.

The mobile phase of the real-time dilution is purified water, and the flow rate is 5-20 ml/min.

The target product obtained by a cyclic purification in step 1, which meets the quality requirements, enters to step 2.

Step 2: mobile phases: A2 phase: a 0.1-0.4% ammonium acetate solution, the pH value is 6.5-7.0, B phase: chromatographic grade acetonitrile, the flow rate is 60-80 ml/min, and the detection wavelength is 230 nm.

After the column 1 is rinsed with a more than 50% acetonitrile solution, the product obtained in step 1 is loaded and rinsed with 95% A2 and 5% B for 15-30 min for a desalination. Then a gradient elution is performed for 20 min for salt conversion to collect the target peak product, A2% is 85%-65% and B % is 15%-35%. A collected target peptide solution is rotary evaporated under reduced pressure in a water bath having a water temperature of no more than 32° C. and concentrated to about 15-50 mg/mL and then transferred to a suitable-sized vial. After freeze-drying, the qualified ularitide with a purity more than 99.0% can be obtained.

0.92 g of white powder solid purified peptides is obtained after the freeze-drying. The purity is 99.28%, and the single impurity is less than 0.15%. The yield after purification is 68% (calculated based on the content of ularitide in the crude product), and the total yield is 46%. During the purification process, there is no need to recycle and purify the intermediate. According to the calculation, compared with embodiments 4-5, the waste liquid discharge is reduced by approximately 30% when purifying per unit mass of the crude ularitide due to the reduction of the cycle number in step 1.

Embodiment 2: Purification of Crude Ularitide 15 g of crude ularitide is dissolved and filtered, and a filtrate is collected for use.

1. Purification conditions: chromatographic columns: a chromatographic column filled with a stationary phase C18 silica gel packing with a particle size of 10 μm is used as the column 1, and the diameter and length of the column is 10 cm×15 cm; a chromatographic column filled with a stationary phase C18 silica gel packing with a particle size of 5 μm is used as the column 2, and the diameter and length of the column is 10 cm×10 cm.

Step 1: mobile phases: A1 phase: the pH value of a potassium dihydrogen phosphate solution (150 mmol/L) is adjusted to 2.5 with phosphoric acid; B phase: chromatographic grade acetonitrile; the flow rate is 200-220 ml/min, and the detection wavelength is 230 nm.

A linear crude ularitide solution is loaded and eluted for 50-70 min with the following gradient: A %: 85/6-65%, B %: 15%-35%. In the elution process, the waste liquid is discarded if an impurity peak appears during the separation through the chromatographic column 1. When a target product peak comes out, the target product is subjected to a real-time dilution by a third pump connected to a three-way mixer and then enters into the column 2 for a secondary separation.

The mobile phase of the real-time dilution is purified water, and the flow rate is 20-50 ml/min.

The product obtained by a cyclic purification in step 1, which meets the quality requirements, enters to step 2.

Step 2: mobile phases: A2 phase: a 0.1-0.4% ammonium acetate solution, the pH value is 6.5-7.0, B phase: chromatographic grade acetonitrile, the flow rate is 200-220 ml/min, and the detection wavelength is 230 nm.

After the column 1 is rinsed with a more than 50% acetonitrile solution, the product obtained in step 1 is loaded and rinsed with 95% A2 and 5% B for 15-30 min for a desalination. Then, a gradient elution is performed for 20 min for salt conversion to collect the target peak product, A2% is 85%-65% and B % is 15%-35%. A collected target peptide solution is rotary evaporated under reduced pressure in a water bath having a water temperature of no more than 32° C. and concentrated to about 15-50 mg/mL and then transferred to a suitable-sized vial. After freeze-drying, the qualified ularitide with a purity more than 99.0% can be obtained.

7.1 g of white powder solid purified peptides is obtained after the freeze-drying. The purity is 99.30%, and the single impurity is less than 0.10%. The yield after purification is 73.9% (calculated based on the content of ularitide in the crude product), and the total yield is 47.3%. According to the calculation, compared with embodiments 4-5, the waste liquid discharge is reduced by approximately 35% when purifying per unit mass of the crude ularitide due to the reduction of the cycle number in step 1.

Embodiment 3: Purification of Crude Ularitide 25 g of crude ularitide is dissolved and filtered, and a filtrate is collected for use.

1. Purification conditions: chromatographic columns: a chromatographic column filled with a stationary phase C18 silica gel packing with a particle size of 10 μm is used as the column 1, and the diameter and length of the column is 15 cm×15 cm; a chromatographic column filled with a stationary phase C18 silica gel packing with a particle size of 5 μm is used as the column 2, and the diameter and length of the column is 15 cm×10 cm.

Step 1: mobile phases: A1 phase: the pH value of an ammonium sulfate solution (100 mmol/L) is adjusted to 2.8 with phosphoric acid; B phase: chromatographic grade acetonitrile; the flow rate is 450-550 ml/min, and the detection wavelength is 230 nm.

A linear crude ularitide solution is loaded and eluted for 50-70 min with the following gradient: A %: 85/6-65%, B %: 15%-35%. In the elution process, the waste liquid is discarded if an impurity peak appears during the separation through the chromatographic column 1. When a target product peak comes out, the target product is subjected to a real-time dilution by a third pump connected to a three-way mixer and then enters into the column 2 for a secondary separation.

The mobile phase of the real-time dilution is purified water, and the flow rate is 45-100 ml/min.

The product obtained by a cyclic purification in step 1, which meets the quality requirements, enters to step 2.

Step 2: mobile phases: A2 phase: a 0.1-0.4% ammonium acetate solution, the pH value is 6.5-7.0, B phase: chromatographic grade acetonitrile, the flow rate is 450-550 ml/min, and the detection wavelength is 230 nm.

After the column 1 is rinsed with a more than 50% acetonitrile solution, the product obtained in step 1 is loaded and rinsed with 95% A2 and 5% B for 15-30 min for a desalination. Then a gradient elution is performed for 20 min for salt conversion to collect the target peak product, A2% is 85%-65% and B % is 15%-35%. A collected target peptide solution is rotary evaporated under reduced pressure in a water bath having a water temperature of no more than 32° C. and concentrated to about 15-50 mg/mL and then transferred to a suitable-sized vial. After freeze-drying, the qualified ularitide with a purity more than 99.0% can be obtained.

12.1 g of white powder solid purified peptides is obtained after the freeze-drying. The purity is 99.26%, and the single impurity is less than 0.10%. The yield after purification is 67% (calculated based on the content of ularitide in the crude product), and the total yield is 48.4%. According to the calculation, compared with embodiments 4-5, the waste liquid discharge is reduced by approximately 40% when purifying per unit mass of the crude ularitide due to the reduction of the cycle number in step 1.

Embodiment 4: Comparative Example for Purification of Crude Ularitide 25 g of crude ularitide is dissolved and filtered, and a filtrate is collected for use.

1. Purification conditions: chromatographic column: a chromatographic column filled with a stationary phase C18 silica gel packing with a particle size of 10 μm is used as the column 1, and the diameter and length of the column is 15 cm×25 cm.

Step 1: mobile phases: A1 phase: the pH value of an ammonium sulfate solution (100 mmol/L) is adjusted to 2.8 with phosphoric acid; B phase: chromatographic grade acetonitrile; the flow rate is 450-550 ml/min, and the detection wavelength is 230 nm.

A linear crude ularitide solution is loaded and eluted for 50-70 min with the following gradient: A %: 85%-65%, B %: 15/6-35%.

The product obtained by a cyclic purification in step 1, which meets the quality requirements, enters to step 2.

Step 2: mobile phases: A2 phase: a 0.1-0.4% ammonium acetate solution, the pH value is 6.5-7.0, B phase: chromatographic grade acetonitrile, the flow rate is 450-550 ml/min, and the detection wavelength is 230 nm.

After the column 1 is rinsed with a more than 50% acetonitrile solution, the product obtained in step 1 is loaded and rinsed with 95% A2 and 5% B for 15-30 min for a desalination. Then a gradient elution is performed for 20 min for salt conversion to collect the target peak product, A2% is 85%-65% and B % is 15%-35%. A collected target peptide solution is rotary evaporated under reduced pressure in a water bath having a water temperature of no more than 32° C. and concentrated to about 15-50 mg/mL and then transferred to a suitable-sized vial. After freeze-drying, the qualified ularitide with a purity more than 99.0% can be obtained.

8.1 g of white powder solid purified peptides is obtained after the freeze-drying. The purity is 99.30%, and the single impurity is less than 0.10%. The yield after purification is 64% (calculated based on the content of ularitide in the crude product), and the total yield is 32.4%. According to the calculation, when 25 g of the crude peptides is purified, unqualified fractions need to be recovered and purified at least three times to reach the same result as that obtained in embodiment 1. After the production is enlarged, recovery times of the unqualified fractions increases by at least 30%-40%, the amount of acetonitrile used increases by 20%-30%, the amount of waste liquid discharge increases by about 40%, and the cycle increases by 30%.

Embodiment 5: Comparative Example for Purification of Crude Ularitide 25 g of crude ularitide is dissolved and filtered, and a filtrate is collected for use.

1. Purification conditions: chromatographic column 1: a chromatographic column filled with a stationary phase C18 silica gel packing with a particle size of 5 μm is used as the column, and the diameter and length of the column is 15 cm×25 cm.

Step 1: mobile phases: A1 phase: the pH value of an ammonium sulfate solution (100 mmol/L) is adjusted to 2.8 with phosphoric acid; B phase: chromatographic grade acetonitrile; the flow rate is 450-550 ml/min, and the detection wavelength is 230 nm.

A linear crude ularitide solution is loaded and eluted for 50-70 min with the following gradient: A1%: 85%-65%, B %: 15/6-35%.

The product obtained by a cyclic purification in step 1, which meets the quality requirements, enters to step 2.

Step 2: mobile phases: A2 phase: a 0.1-0.4% ammonium acetate solution, the pH value is 6.5-7.0, B phase: chromatographic grade acetonitrile, the flow rate is 450-550 ml/min, and the detection wavelength is 230 nm.

After the column 1 is rinsed with a more than 50% acetonitrile solution, the product obtained in step 1 is loaded and rinsed with 95% A2 and 5% B for 15-30 min for a desalination. Then a gradient elution is performed for 20 min for salt conversion to collect the target peak product, A2% is 85%-65% and B % is 15%-35%. A collected target peptide solution is rotary evaporated under reduced pressure in a water bath having a water temperature of no more than 32° C. and concentrated to about 15-50 mg/mL and then transferred to a suitable-sized vial. After freeze-drying, the qualified ularitide with a purity more than 99.0% can be obtained.

8.3 g of white powder solid purified peptides is obtained after the freeze-drying. The purity is 99.30%, and the single impurity is less than 0.10%. The yield after purification is 64% (calculated based on the content of ularitide in the crude product), and the total yield is 33.2%. According to the calculation, the amount of acetonitrile used increases by 15%, the amount of waste liquid discharge increases by about 35%, and the cycle increases by 20%. However, in the preparation process, the distillate is precipitated in the storage process, and the dissolution is difficult. Moreover, during preparation, the column pressure is high, which is close to the upper limit of the preparation system. 5 μm reversed-phase packing is not recommended for use and its cost is also high.

Embodiment 6: Comparative Example for Purification of Crude Ularitide 25 g of crude ularitide is dissolved and filtered, and a filtrate is collected for use.

1. Purification conditions: chromatographic columns: a chromatographic column filled with a stationary phase C18 silica gel packing with a particle size of 10 μm is used as the column 1, and the diameter and length of the column is 15 cm×15 cm; a chromatographic column filled with a stationary phase C18 silica gel packing with a particle size of 10 μm is used as the column 2, and the diameter and length of the column is 15 cm×10 cm.

Step 1: mobile phases: A1 phase: the pH value of an ammonium sulfate solution (100 mmol/L) is adjusted to 2.8 with phosphoric acid; B phase: chromatographic grade acetonitrile; the flow rate is 450-550 ml/min, and the detection wavelength is 230 nm.

A linear crude ularitide solution is loaded and eluted for 50-70 min with the following gradient: A %: 85/6-65%, B %: 15%-35%. In the elution process, the waste liquid is discarded if an impurity peak appears during the separation through the chromatographic column 1. When a target product peak comes out, the target product is subjected to a real-time dilution by a third pump connected to a three-way mixer and then enters into the column 2 for a secondary separation.

The mobile phase of the real-time dilution is purified water, and the flow rate is 45-100 ml/min.

The product obtained by a cyclic purification in step 1, which meets the quality requirements, enters to step 2.

Step 2: mobile phases: A2 phase: a 0.1-0.4% ammonium acetate solution, the pH value is 6.5-7.0, B phase: chromatographic grade acetonitrile, the flow rate is 450-550 ml/min, and the detection wavelength is 230 nm.

After the column 1 is rinsed with a more than 50% acetonitrile solution, the product obtained in step 1 is loaded and rinsed with 95% A2 and 5% B for 15-30 min for a desalination. Then a gradient elution is performed for 20 min for salt conversion to collect the target peak product, A2% is 85%-65% and B % is 15%-35%. A collected target peptide solution is rotary evaporated under reduced pressure in a water bath having a water temperature of no more than 32° C. and concentrated to about 15-50 mg/mL and then transferred to a suitable-sized vial. After freeze-drying, the qualified ularitide with a purity more than 99.0% can be obtained.

8.52 g of white powder solid purified peptides is obtained after the freeze-drying. The purity is 99.24%, and the single impurity is less than 0.10%. The yield after purification is 64% (calculated based on the content of ularitide in the crude product), and the total yield is 34.1%. According to the calculation, compared with embodiment 4, the waste liquid discharge is reduced by approximately 5% when purifying per unit mass of the crude ularitide due to the reduction of the cycle in step 1 by about 10%. When the particle size is large, the advantages of connecting columns with the same packing in series are not significant.

Embodiment 7: Comparative Example for Purification of Crude Ularitide 25 g of crude ularitide is dissolved and filtered, and a filtrate is collected for use.

1. Purification conditions: chromatographic columns: a chromatographic column filled with a stationary phase C18 silica gel packing with a particle size of 5 μm is used as the column 1, and the diameter and length of the column is 15 cm×15 cm; a chromatographic column filled with a stationary phase C18 silica gel packing with a particle size of 5 μm is used as the column 2, and the diameter and length of the column is 15 cm×10 cm.

Step 1: mobile phases: A1 phase: the pH value of an ammonium sulfate solution (100 mmol/L) is adjusted to 2.8 with phosphoric acid; B phase: chromatographic grade acetonitrile; the flow rate is 450-550 ml/min, and the detection wavelength is 230 nm.

A linear crude ularitide solution is loaded and eluted for 50-70 min with the following gradient: A %: 85/6-65%, B %: 15%-35%. In the elution process, the waste liquid is discarded if an impurity peak appears during the separation through the chromatographic column 1. When a target product peak comes out, the target product is subjected to a real-time dilution by a third pump connected to a three-way mixer and then enters into the column 2 for a secondary separation.

The mobile phase of the real-time dilution is purified water, and the flow rate is 45-100 ml/min.

The product obtained by a cyclic purification in step 1, which meets the quality requirements, enters to step 2.

Step 2: mobile phases: A2 phase: a 0.1-0.4% ammonium acetate solution, the pH value is 6.5-7.0, B phase: chromatographic grade acetonitrile, the flow rate is 450-550 ml/min, and the detection wavelength is 230 nm.

After the column 1 is rinsed with a more than 50% acetonitrile solution, the product obtained in step 1 is loaded and rinsed with 95% A2 and 5% B for 15-30 min for a desalination. Then a gradient elution is performed for 20 min for salt conversion to collect the target peak product, A2% is 85%-65% and B % is 15%-35%. A collected target peptide solution is rotary evaporated under reduced pressure in a water bath having a water temperature of no more than 32° C. and concentrated to about 15-50 mg/mL and then transferred to a suitable-sized vial. After freeze-drying, the qualified ularitide with a purity more than 99.0% can be obtained.

8.9 g of white powder solid purified peptides is obtained after the freeze-drying. The purity is 99.24%, and the single impurity is less than 0.10%. The yield after purification is 66% (calculated based on the content of ularitide in the crude product), and the total yield is 35.6%. According to the calculation, compared with embodiment 5, using the same packing with small particle size, the removal effect of some impurities is better, while the removal effect of some other impurities is weaker. Overall, the waste liquid discharge is reduced by approximately 15% when purifying per unit mass of the crude ularitide due to the reduction of the cycle number in step 1 by about 20%. However, the cost of packings increases by 30%, and overall, the advantages are not significant.

Embodiment 8: Purification of Crude Semaglutide 15 g of crude semaglutide is dissolved and filtered, and a filtrate is collected for use.

1. Purification conditions: chromatographic columns: a chromatographic column filled with a stationary phase C8 silica gel packing with a particle size of 10 μm is used as the column 1, and the diameter and length of the column is 15 cm×10 cm; a chromatographic column filled with a stationary phase C4 silica gel packing with a particle size of 5 μm is used as the column 2, and the diameter and length of the column is 15 cm×10 cm.

Step 1: mobile phases: A1 phase: the pH value of an ammonium bicarbonate solution (100 mmol/L) is adjusted to 8.0 with tetramethyl ammonium hydroxide; B phase: chromatographic grade acetonitrile:isopropanol=9:1; the flow rate is 450-550 ml/min, and the detection wavelength is 230 nm.

A crude semaglutide solution is loaded and eluted for 50-70 min with the following gradient: A %: 85%-65%, B %: 15%-35%. In the elution process, the waste liquid is discarded if an impurity peak appears during the separation through the chromatographic column 1. When a target product peak comes out, the target product is subjected to a real-time dilution by a third pump connected to a three-way mixer and then enters into the column 2 for a secondary separation.

The mobile phase of the real-time dilution is purified water, and the flow rate is 50-70 ml/min.

The product obtained by a cyclic purification in step 1, which meets the quality requirements, enters to step 2.

Step 2: mobile phases: A2 phase: a 0.1-0.4% ammonium acetate solution, the pH value is 6.5-7.0, B phase: chromatographic grade acetonitrile, the flow rate is 450-550 ml/min, and the detection wavelength is 230 nm.

After the column 1 is rinsed with a more than 50% acetonitrile solution, the product is loaded and rinsed with the 0.1-0.4% ammonium acetate solution (pH 6.5-7.0) containing 5% acetonitrile for 15-30 min. Then a gradient elution is performed for 40 min to collect the target peak product, the gradient of acetonitrile: B % is 40%-60%. A collected target peptide solution is rotary evaporated under reduced pressure in a water bath having a water temperature of no more than 32° C. and concentrated to about 15-50 mg/mL and then transferred to a suitable-sized vial. After freeze-drying, the qualified semaglutide with a purity more than 99.0% can be obtained.

4.1 g of white powder solid purified peptides is obtained after the freeze-drying. The purity is 99.32%, and the single impurity is less than 0.15%. The yield after purification is 57% (calculated based on the content of semaglutide in the crude product), and the total yield is 27.3%. After being connected in series, the waste liquid discharge is reduced by 35% and the cycle is reduced by 25%.

Embodiment 9: Purification of Crude Liraglutide 15 g of crude liraglutide is dissolved and filtered, and a filtrate is collected for use.

1. Purification conditions: chromatographic columns: a chromatographic column filled with a stationary phase C18 silica gel packing with a particle size of 10 μm is used as the column 1, and the diameter and length of the column is 15 cm×15 cm; a chromatographic column filled with a stationary phase C4 silica gel packing with a particle size of 5 μm is used as the column 2, and the diameter and length of the column is 15 cm×15 cm.

Step 1: mobile phases: A1 phase: the pH value of an ammonium bicarbonate solution (100 mmol/L) is adjusted to 8.0 with ammonium hydroxide; B phase: chromatographic grade acetonitrile:isopropanol=9:2, the flow rate is 450-550 ml/min, and the detection wavelength is 230 nm.

A crude liraglutide solution is loaded and eluted for 50-70 min with the following gradient: A %: 70%-55%, B %: 30%-45%. In the elution process, the waste liquid is discarded if an impurity peak appears during the separation through the chromatographic column 1. When a target product peak comes out, the target product is subjected to a real-time dilution by a third pump connected to a three-way mixer and then enters into the column 2 for a secondary separation.

The mobile phase of the real-time dilution is purified water, and the flow rate is 50-100 ml/min.

The product obtained by a cyclic purification in step 1, which meets the quality requirements, enters to step 2.

Step 2: mobile phases: A2 phase: a 0.1-0.4% ammonium acetate solution, the pH value is 6.5-6.8, B phase: chromatographic grade acetonitrile, the flow rate is 450-550 ml/min, and the detection wavelength is 230 nm.

After the column 1 is rinsed with a more than 50% acetonitrile solution, the product is loaded and rinsed with the 0.1-0.4% ammonium acetate solution containing 5% acetonitrile for 15-30 min. Then a gradient elution is performed for 30 min to collect the target peak product, the gradient of acetonitrile: B % is 40/6-60%. A collected target peptide solution is rotary evaporated under reduced pressure in a water bath having a water temperature of no more than 32° C. and concentrated to about 50 mg/mL and then transferred to a suitable-sized vial. After freeze-drying, the qualified liraglutide with a purity more than 99.0% can be obtained.

3.8 g of white powder solid purified peptides is obtained after the freeze-drying. The purity is 99.32%, and the single impurity is less than 0.15%. The yield after purification is 52% (calculated based on the content of liraglutide in the crude product), and the total yield is 25.3%. After being connected in series, the waste liquid discharge is reduced by 30% and the cycle is reduced by 25%.

What is claimed is:

1. A method for purifying a polypeptide, comprising the following steps:
    1) purification step: connecting an upstream chromatographic column and a downstream chromatographic column in series to separate a crude product, wherein a packing in the upstream chromatographic column and a packing in the downstream chromatographic column in step 1) are at least one silica gel packing selected from the group consisting of C18 silica gel packing, C8 silica gel packing, and C4 silica gel packing, or a polymer packing; a length of the upstream chromatographic column is 8-20 cm; a length of the downstream chromatographic column is 8-20 cm;
    mobile phases in step 1): A1 phase is a buffered salt solution with a pH value of 2-3; and the buffered salt solution is at least one salt selected from the group consisting of ammonium sulfate, potassium dihydrogen phosphate, disodium hydrogen phosphate and dipotassium hydrogen phosphate; B phase is a first organic phase, and the first organic phase is at least one selected from the group consisting of acetonitrile, methanol, isopropanol and ethanol; and a molar concentration of the salt in the buffered salt solution is 20 mM-150 mM;
    step 1) comprises a first gradient elution: A1 phase %: 95%-55%, and a balance for B phase %, and an elution time is 30-120 min; in the first gradient elution, when an outflow peak of the upstream chromatographic column is an impurity peak, a corresponding mobile phase is discarded; when the outflow peak of the upstream chromatographic column is a target peak, a chromatographic pump connected to a three-way mixer arranged tween the upstream chromatographic column and the downstream chromatographic column is opened, purified water is inputted to the three-way mixer to perform a real-time dilution, and then a target peak product enters into the downstream chromatographic column for a secondary separation after the real-time dilution to obtain a purified target peak product;

the method for purifying the polypeptide further comprises step 2) of a salt conversion:

step 2): using the upstream chromatographic column in step 1) for the salt conversion, wherein, in the mobile phases of step 2), A2 phase is an acetic acid aqueous solution with a volume ratio of acetic acid/water of 0.05%-0.2%, and B phase is a second organic phase, and the second organic phase is acetonitrile;

step 2) comprises: loading the purified target peak product obtained in step 1) onto the upstream chromatographic column and rinsing the purified target peak product with 95% of the A2 phase and 5% of the B phase for 15-30 min for a desalination;

then performing a second gradient elution for 10-30 min for the salt conversion to collect a target product; A2 phase %: 95%-55%, and a balance for B phase %.

2. The method according to claim 1, wherein the polypeptide is one selected from the group consisting of ularitide, liraglutide, semaglutide, thymalfasin, abaloparatide and lixisenatide.

3. The method according to claim 1, wherein, in step 1), the packing in the upstream chromatographic column is the C18 silica gel packing having a particle size of 10 μm, and the length of the upstream chromatographic column is 10-15 cm; and the packing in the downstream chromatographic column is the C18 silica gel packing having a particle size of 5 μm, and the length of the downstream chromatographic column is 10-15 cm.

4. The method according to claim 1, wherein step 1) comprises the first gradient elution: the A1 phase %: 85%-65%, and the balance for the B phase %, and the elution time is 50-70 min.

5. The method according to claim 1, wherein the real-time dilution is as follows: before the target peak product enters the downstream chromatographic column, an amount of the purified water is inputted through the chromatographic pump to reduce a ratio of the first organic phase in the outflow peak entering the downstream chromatographic column; and the amount of the purified water is 10% volume of the outflow peak.

6. The method according to claim 1, wherein the pH value of the A1 phase is 2.2-2.8.

7. The method according to claim 1, wherein the A2 phase is an ammonium acetate aqueous solution with a volume ratio of ammonium acetate/water of 0.1%-0.4%.

8. The method according to claim 1, wherein, in step 2), the second gradient elution is performed for 10-30 min for the salt conversion to collect the target product; the A2 phase %: 85%-65%, the B phase %: 15%-35%.

* * * * *

```
                        SEQUENCE LISTING

<160> NUMBER OF SEQ ID NOS: 1

<210> SEQ ID NO 1
<211> LENGTH: 32
<212> TYPE: PRT
<213> ORGANISM: Homo sapiens

<400> SEQUENCE: 1

Thr Ala Pro Arg Ser Leu Arg Arg Ser Ser Cys Phe Gly Gly Arg Met
1               5                   10                  15

Asp Arg Ile Gly Ala Gln Ser Gly Leu Gly Cys Asn Ser Phe Arg Tyr
            20                  25                  30
```